United States Patent [19]

Wang et al.

[11] Patent Number: 5,419,079

[45] Date of Patent: May 30, 1995

[54] METHOD OF PRODUCING VIRUS FREE POTATO MINITUBERS

[75] Inventors: Bingjun Wang; Luye Wang; Xiaohui Liu, all of Tianjin, China

[73] Assignee: Tianjin Research Institute of Vegatable, Tianjin, China

[21] Appl. No.: 177,573

[22] Filed: Jan. 5, 1994

[30] Foreign Application Priority Data

Jan. 7, 1993 [CN] China .................. 93100096.3

[51] Int. Cl.$^6$ .................. A01B 79/00; C12N 5/00
[52] U.S. Cl. .................. 47/58; 47/DIG. 3; 435/240.51; 435/240.45; 504/116
[58] Field of Search .................. 800/200, DIG. 40, 42; 435/240.45, 240.4, 240.54, 240.51; 47/58, DIG. 3

[56] References Cited

PUBLICATIONS

Wang et al. 1982 American Potato Journal 59(133–37.

Zaag. 1987. In Viruses of potatoes and seed–potato production. de Bokx et al., eds. ch. 13:176–203.

*Primary Examiner*—David T. Fox
*Assistant Examiner*—Erich E. Veitenheimer
*Attorney, Agent, or Firm*—Ladas & Parry

[57] ABSTRACT

This invention discloses a method of producing virus-free potato minitubers, which includes the steps of selecting virus-free test-tube plantlets and stem sections cut from seedlings grown 30 days after cuttage of such virus-free test-tube plantlets as cuttaging seedlings, choosing vermiculite as cuttage medium, treating the cuttaging seedlings with plant growth regulators, keeping the growth conditions of the cuttaging seedlings at 25° C. during the daytime and 12°–17° C. at night, relative humidity 95–100% during the early stage and 60–70% at the later stage, and a light duration of ten hours a day with illuminance of 400–600 lux, along with suitable field management of water and fertilizer. The virus-free potato minitubers can be harvested in 30 to 60 days.

9 Claims, No Drawings

METHOD OF PRODUCING VIRUS FREE POTATO MINITUBERS

FIELD OF THE INVENTION

This invention relates to a method of producing virus.-free potato minitubers, especially a method of producing a virus-free potato minituber using the combination of potato stem-tip virus elimination, rapid propagation and soilless cultivation techniques.

BACKGROUND OF THE INVENTION

At present, techniques such as using shoot tips and axillary buds of potato and using cutting sections of young plantlets for propagating plantable virus-free seedlings and further producing virus-free potato minitubers have been adopted. There are a number of publications dealing with the production of virus-free potato minitubers.

Chinese Patent Application No. 87106041.8 disclosed a mass production of viroid-free and virus-free potato propagation material, which included separating tissue cells from potato stem-tips, culturing them in nutrient medium, and then inducing them to take roots or microtubers. The following is the detailed procedure: culturing the virus-free test-tube plantlets in a liquid without nutrient at 22° C. and 3000 lux in culture flasks numbered by plants, after about three weeks, replacing the liquid in the flasks by a nutrient solution to accelerate tuberization(which consists of phenyladenine 10 mg/l, coumarin 10 mg/l, sucrose 8% and some inorganic nitrogen source etc.), culturing them at 17° C. and 1000 lux for another 10–12 weeks. 40–60 potato microtubers with 0.3–0.6 cm in diameter are thus developed. The procedure for minitubers is as follows: planting the microtubers above in a mixture of peat and pearlite containing 0.5 Kg/m$^2$ of urea at the density of 400 plants per square meter, watering the plants under natural temperature and illumination, after eight weeks adding a plant growth regulator (a chlorine-choline-chloride) to inhibit the growth of leaves and, at the same time, stopping watering 3–4 minituber stocks with 0.5–2.0 cm in diameter are thus obtained. The disadvantages of this method are long growth period, namely 10–12 weeks for microtubers and 85–90 days for minitubers, and, accordingly, high cost of production. In addition, the whole process is conducted in a laboratory and a lot of organic compounds are consumed. Therefore, it is not suitable for practical mass production and has high cost.

Chinese Patent Application No. 89106287.4 disclosed a method of propagating and planting potatoes, which included cutting test-tube plantlets into sections with an axillary bud on each section, treating the stem section under the leaf with growth and rooting-accelerating compounds and then transplanting the sections into nutrient medium within rolled plastic film, (the nutrient medium is made of tiny peat from marshland with adding fertilizer and trace or common elements such as (NH$_4$)$_3$PO$_4$, NH$_4$NO$_3$, K$_2$SO$_4$, MgSO$_4$, Fe$_2$(SO$_4$)$_3$, CuSO$_4$, ZnSO$_4$, HBO$_3$, NH$_4$MO$_4$, rock powder etc. and its pH is adjusted to 5.0–5.5), spraying water onto the peat and covering the film rolls with polyethylene film, keeping the plants so growing for another 20–25 days. 4–6 sections can be cut from each plant and be transplanted into film rolls when further propagation is wanted. Plantlets with well developed roots can be obtained directly from these sections growing in film rolls and be transplanted into open field to produce potato tubers. 40–50 tubers with the average weight of 25–29 g can then be produced from each plant. The disadvantages of this method are huge propagation of seedlings and large spaces needed for them, inconvenience of management, high production cost and inconvenient long distance transport of lots of seedlings as well.

Chinese Patent Application No. 90101337.4 disclosed a mass production method of seed potatoes (potato microtubers), which was an improved method of mass production of pathogen-free seed potatoes (potato microtubers) by tissue culture technique of plant, producing test-tube plantlets in flat-bottomed culture disks with the disadvantages of long growth cycle, very high production cost and smaller microtubers.

OBJECT OF THE INVENTION

The object of the present invention is to overcome the drawbacks in existing potato minituber production technique and provide a method of producing virus-free potato minitubers with the advantages of extensive seedling source, high survival rate, low preparation cost, high propagation speed and microminiaturization of the seed tubers.

SUMMARY OF THE INVENTION

This invention provides a method of producing virus-free potato minitubers, which includes cultivating virus-free test tube plantlets, selecting them and the plantlets after their cuttage and growth as cuttaging seedlings, preparing soiless culture medium and seedling trays, treating the cutting sections with plant growth regulator solution, cuttaging the cuttaging seedlings, postmanaging and controlling of temperature, illuminance, water, air and fertilizer, and harvesting the seed potatoes after 30–60 days.

The method according to the present invention has advantages of fast propagation of seed tubers, less space occupied (900–1100 tubers per square meter), larger size (average diameter 1.15–1.20 cm) and heavier average weight (above 0.6–1.0 g) of the seed tubers, healthy (virusfree), good applicability (they can be directly planted in open field to propagate stock tubers) and easy storage and transportation.

The method according to the present invention is suitable for mass plant-scale production with simple equipment, easy operation and management, less labor, less consumption of water and fertilizer, lower production cost, no limitation to seasons and geographic circumstances such as elevation and latitude, extensive seedling sources, sharply shortened production period and worldwide applicability.

DETAILED DESCRIPTION OF THE INVENTION

This invention relates to a method of producing virus-free potato minitubers, which includes the following steps:

1. using the existing virus-elimination technique and culturing virus-free plantlets in test-tubes, selecting healthy test tube seedlings aged 20–40 days as cuttaging seedling source;

2. selecting vermiculite 4# as cuttaging medium, sufficiently immersing the plantlets in water or de-ionized water one day before cuttaging and then filtering out the surplus water, piling the plantlets naturally on seedling trays, in which the thickness of the cuttaging medium is 4–7 cm, and leveling off the cuttage medium;

3. cutting the virus-free test tube plantlets in step 1 into stem sections with one or two nodes on each section as cuttaging seedlings;

4. immersing the lower part of the cuttaging seedlings obtained in step 3 in plant growth regulator solution containing 10–100 ppm TSA, 0.1–1.5 ppm GA-3 and 100–3000 ppm $KH_2PO_4$ for 5–30 minutes;

5. gripping the lower part of the cuttaging seedlings treated in step 4 with sterilized tweezers and cuttaging them gently into the medium in seedling tray with spacing of 2–3 * 2–3 cm between each plant and line, leaving the leaves of the cuttaging seedlings above the surface of the medium;

6. placing the cuttaged seedling trays into an arched shed built with frames and plastic film in a green house, keeping the environment within the shed at relative humidity 90–100%, temperature 23°–28° C. during daytime and 12°–17° C. at night, light duration 10 hours a day with an illuminance of 400–600 lux, and 60–70% of the relative humidity in the green house;

7. watering with fresh water once a day during the first 5–7 days and changing to once or twice a day afterwards with nutrient solution containing $KNO_3$ 9–12 g, $KH_2PO_4$ 3–4 g, $Ca(NO_3)_2$ 0.8–1.6 g, $NH_4NO_3$ 1.5–3.0 g, $MgSO_4$ 4–6 g, $FeSO_4$ 0.2–0.4 g, di-sodium EDTA 0.3–0.5 g in every ten liters with a pH range 5.5–6.5;

8. after 8–10 days from cuttage, gradually opening up the plastic film which covers the shed, and another 2–3 days later, leaving the seedling trays open in the green house for open culturing;

9. spraying a solution containing 50–200 ppm of TSP plant growth regulator onto the leaves of potato seedlings in seedling trays after ten days from cuttage, and then spraying the solution once every seven days for accelerating tuberization;

10. harvesting the virus-free potato minitubers after 30–60 days of culturing according to the conditions above. The average diameter of the seed tubers is 1.0–1.3 cm, with average weight of 0.6–1.2 g. 900–1100 minitubers can be harvested from each one square meter of seedling trays.

According to the method of this invention, the cuttaging seedlings can also be the new plantlets, called plantlet B afterwards, growing up by cutting away the upper stem sections from said virus-free test tube plantlets (called plantlet A later on) and culturing the left lower stem sections with a node on each in test-tubes for 18–20 days. The preferred cuttaging seedlings in the invention are plantlets B.

According to the method of this invention, the cuttaging seedlings can further be the stem tip (called plantlet C afterwards) cut from the developed seedlings of plantlet A or plantlet B (as cuttaging seedlings) after 30 days growth in accordance with the method of the invention mentioned above. The more preferred cuttaging seedlings of the invention are plantlets C because they are in plentiful supply, and have high survival rate after cuttage and shorter period of tuberization.

The preferred plant growth regulators solution in the invention is an aqueous solution containing 0.5 ppm GA-3, 20 ppm TSA and 3000 ppm $KH_2PO_4$, or an aqueous solution containing 100 ppm TSP, 0.5 ppm GA-3, 20 ppm TSA and 3000 ppm $KH_2PO_4$. The soaking period of the cuttaging seedlings, including plantlet A, B and C, in the plant growth regulator aqueous solution should be 10–15 min.

In this specification, GA-3 is the trade mark of gibberellin made in Shanghai Solvent Factory; TSA is indolylbutyric acid for accelerating rootage; TSP is a sweller manufactured in Jiangsu Huaiyin Fertilizer Plant.

This invention also deals with virus-free potato minitubers produced in accordance with the method of this invention.

The favorable feature of this invention is to broaden the cuttaging seedling source, i.e. plantlet A, B and C mentioned above.

Plantlet A is the virus-free test tube plantlet cultivated according to conventional technique, which can either provide seedling source for preservation of potato variety or produce seed potatoes after cuttage. Plantlet A, for example, can be obtained as follows:

Cut the selected potato tuber into chunks and plant them in sand trays. After sprouting, take the 1–2 cm young buds out and put them in a flask to wash them for one hour. Then, place them into a germ-free chamber for strict sterilization with 95% ethanol immersion for a little while firstly, then 5% of sodium hypochlorite solution for 3–10 minutes and finally rinsing with germ-free water 3–4 times. Cut and take 4–5 mm stem tip with a dissecting scalpel under a dissecting glass and transplant it into a culture medium in a test tube for culturing. After 30 days, cut and take stem-tip meristem with 1–2 axillary buds leaf primordium with a dissecting scalpel under superclean table and transplant it to test tubes filled with MS culture medium for cultivation. Place the test tubes with transplanted stem-tip meristem on the culture shelf. Culture them under 25° C. during the daytime, 15° C. at night and 3000 lux of illuminance in the culture chamber for one and a half months and the stem-tip seedlings are thus obtained.

Conduct virus inspection to stem-tip seedlings formed above by conventional biological inspection methods and antiserum method and conduct propagation culturing of the definitely virus-free stem-tip seedlings according to the following method to produce virus-free test tube plantlets:

1. Preparation of culture medium:
adding 100 ml MS culture medium to 900 ml water, mixing homogeneously, adding 7 g agar under heating and dissolving it in the solution, then adding 20 g sucrose and dissolving, adjusting its pH to about 5.8, pouring this culture medium solution into 50 ml test tubes for 10 ml each, sealing them with flask covers and sterilizing them under 1.11 $Kg/cm^2$ pressure for 20 minutes;

2. Transferring and inoculating:
transferring and inoculating the virus-free stem-tip seedlings into sterilized test tubes filled with culture medium under superclean table;

3. culturing the test tubes with inoculated stem-tip seedlings at 22°–24° C. and 3000 lux illuminance in a culture chamber for 20–40 days. Virus-free test tube plantlets are thus obtained.

Plantlets B, according to this invention, are the branches grown from the lower stem sections remaining in the culture medium in test tubes after cutting off plantlet A, which can act as cuttaging seedlings for cuttage after 20 day cultivation. Because all plantlets B possess growable points, they have a high survival rate and growth rate after cuttage. Accordingly, with plantlets B as cuttaging seedlings, not only the seedling source is widened, but also the production cost is reduced.

The particularly favorite feature of the invention is that plantlet C is introduced as cuttaging seedling source, i.e. after cuttage of plantlet A and B and growth for 20 days, cut and take the stem sections with growable points as cuttaging seedlings.

Plantlets C have the unique characterized of high survival rate, good resistance-stress and early tuberization. Its tuberization period can be shortened to 30–40 days with large tuber size and uniform shape. The weight of every one hundred tubers is increased by 30–40%. Thus, plantlet C is the major seedling source for plant-scale production.

Owing to the three-step-culturing and application of plantlet A, B,and C successively in accordance with the invention, the culturing of cuttaging seedlings is turned to open style gradually from germ-free conditions, which can not only provide massive cuttaging seedlings in a short period, efficient seedling source for mass and plant-scale production and greatly shortened production cycle of seed potatoes, but also can further reduce production cost by less consumption of labor, materials and equipment.

The nutrient solution, according to the invention, is preferably the solution containing 0.28 g $FeSO_4$, 0.37 g di-sodium EDTA, 1.7 g $NH_4NO_3$, 10.3 g $KNO_3$, 1 g $Ca(NO_3)_2$, 3.5 g $KH_2PO_4$ and 4.0 g $MgSO_4$ in every 10 liters with pH of 5.8.

The plant growth regulators used in the invention can accelerate rootage of the cuttaging seedlings and the growth, development and tuberization of the young plantlets. The regulator especially accelerate early rootage and increase the number of roots, such as the rootage rate of the cuttaging seedlings, which can be is increased up to 30–33.5% in only three days and 96.7–100% in five days after the treatment of plant growth regulators.

The cuttage medium can also be the mixture of 1:1 vermiculite 4# and weed charcoal in accordance with the method of the invention.

According to this invention, 1600 ppm cycocel solution can be sprayed once every 5–7 days and accumulated 2–3 times, if plantlets over-grow, for regulating the growth of the plantlets and speeding up tuberization.

In this invention, the illumination duration can be conveniently controlled by placing a layer of opaque material on the plastic arched shed.

The method of this invention is further illustrated in details through the following examples.

EXAMPLE 1

In this example, variety Norland potato seed tubers are used. After cutting off stem-tips and culturing them in accordance with existing techniques mentioned above, culture the seedlings in test tubes for 28 days with the method mentioned above to get virus-free test tube plantlets with 8–12 nodes, then, cut off the seedlings above the surface of culture medium in test tubes on a bench located under super-clean table as cuttaging plantlets A being used in this example. Culture again the remaining part leaving in test tubes in culture chamber at the same conditions.

Select larger granular particles of vermiculite 4# as cuttage medium. Sufficiently immerse the medium with tap water one day before cuttage and then pile them naturally in seedling trays with a porous bottom and 60 * 24 * 6 cm in dimension. Scrape the surface of medium with a piece of board and leave it standing-by for later use.

Cut the virus-free test tube plantlets cultured in said test tubes into several stem sections with two nodes on each. Immerse each lower portion of the stem sections in plant growth regulators solution containing 20 ppm of indo lylbutyric acid, 0.5 ppm gibberellin and 500 ppm $KH_2PO_4$ for 15 minutes.

Grip the lower stem sections of the cuttaging seedlings treated above with a pair of sterilized tweezers and cuttage them gently into vermiculite medium in seedling trays with spacing of 2–3 * 2–3 cm each plant and line, leaving the leaves of cuttaging seedlings above the surface of the cuttage medium. Spray water once and place them in an arched shed built with wire and plastic film within a green house. Cover the plastic film with a layer of black cloth to control light duration by alternatively bright and dark in the shed.

For the first seven days after cuttage, close the arched shed and water the cuttaging seedlings once a day to keep the relative humidity in the shed at 98%, the temperature in the green house at 25° C. during daytime and 14°–15° C. at night. Control the light cycle at 10 hours illumination and 14 hours dark every day (24 hours) by opening or closing the black cloth on the shed and control the illuminance at 500 lux. The relative humidity in the green house is kept at 65%.

Take off the plastic film on the shed gradually beginning from the eighth day after cuttage until the tenth day to let the seedling trays completely open, culturing in the green house.

Spray the cuttaging seedlings twice a day from the eighth day after cuttage with nutrient solution containing 10 g $KNO_3$, 1.7 g $NH_4NO_3$, 4.9 g $MgSO_4$, 3.5 g $KH_2PO_4$, 0.28 g $FeSO_4$, 0.37 g di-sodium EDTA and 1 g $Ca(NO_3)_2$ in every 10 liters.

Spray 100 ppm TSP-containing aqueous solution once onto the leaves in the seedling trays on the tenth day after cuttage and spray once every seven days later on.

After 30 days of culturing at conditions mentioned above, cut stem tip with two nodes on each from developed seedlings as the cuttaging seedlings (plantlet C) in the following examples. Continue to culture these plantlets C at the same conditions for 28 days. Then, the seed potatoes can be harvested at 980 tubers per square meter with the weight of 72 grams per 100 tubers and average diameter of 1.0 cm.

EXAMPLE 2

After cutting off upper stem sections from virus-free test tube plantlets in Example 1, continue to culture the lower sections with nodes in culture medium within test tubes for 20 days. Take thus developed seedlings as cuttaging seedlings (plantlet B). Cuttaging and culturing plantlets B as the same method as in Example 1. Stop watering and fertilizing and harvest tubers in 50 days. 1047 tubers can be harvested from every square meter in this Example with the weight of 89 g per 100 tubers and the average diameter of 1.10 cm.

EXAMPLE 3

Take stem sections with two nodes on each, cut from the plantlets developed in 30 day culturing of plantlets A in Example 1 as cuttaging seedlings in this Example (plantlet C). Culture them with the same method as in Example 1. Stop watering and fertilizing and harvest tubers in 40 days. 1156 minitubers of seed potatoes can be harvested from every square meter in this Example with the weight of 95 g per 100 tubers and the average diameter of 1.15 cm.

EXAMPLE 4

Potato variety Norkotar is used in this Example. Conduct the experiment with the same conditions as in Example 1, except 1:1 mixture of vermiculite 4# and weed charcoal as cuttage medium and not cut stem sections from 30 days developed cuttaging seedlings as new cuttaging seedlings. Stop watering and fertilizing and harvest tubers in 53 days. 2745 grams of seed potatoes can be harvested from every square meter in this Example with total 1185 tubers.

What we claimed is:

1. A method of producing virus-free potato minitubers, which includes the following steps:

(1) culturing, using a virus elimination technique, virus-free plantlets in test tubes for use as a cuttaging seedling source;

(2) selecting granular vermiculite 4# as cuttage medium, sufficiently immersing the plantlets in tap or de-ionized water one day before cuttage and then filtering out the surface water, piling the plantlets naturally on seedling trays, in which the thickness of the cuttage medium is 4–7 cm, and leveling off the cuttage medium after completing the piling;

(3) cutting the virus-free test tube plantlets in Step 1 into stem sections with one or two nodes on each section as cuttaging seedlings;

(4) immersing the lower sections of the cuttaging seedlings obtained in Step 3 in an aqueous solution of plant growth regulator containing 10–100 ppm indolylbutyric acid, 0.1–15 ppm GA-3 and 100–3000 ppm $KH_2PO_4$ for 5–30 minutes;

(5) gripping the lower stem sections of the cuttaging seedlings treated in Step 4 with a pair of sterilized tweezers and cuttaging them gently into cuttage medium in seedling trays with spacing of 2–3×2–3 cm. between each plant and line, leaving the leaves of the cuttaging seedlings above the surface of the cuttage medium;

(6) placing the cuttaged seedling trays into an arched shed built by frames and plastic film in a greenhouse, keeping the environment within the shed in relative humidity 90–100%, temperature 23°–28° C. during daytime and 12°–17° C. at night, light cycle 10 hours and 14 hours dark every day with an illuminance of 400–600 lux and a relative humidity in the greenhouse of 60–70%;

(7) watering with fresh water once a day during the first 5–8 days and changing to once or twice a day afterwards with nutrient solution containing $KNO_3$ 9–12 g, $KH_2PO_4$ 3–4 g, $Ca(NO_3)_2$ 0.8–1.6 g, $NH_4NO_3$ 1.5–3.0 g, $MgSO_4$ 4–6 g, $FeSO_4$ 0.2–0.4 g, di-sodium EDTA 0.3–0.5 g in every ten liters with a pH range 5.5–6.5;

(8) after 7–10 days from cuttage, gradually opening up the plastic film, which covered the shed, and another 2–3 days later, leaving the seedling trays opened in the greenhouse for open culturing;

(9) spraying a solution containing 50–200 ppm of TSP plant growth regulator under the leaves of potato seedlings in seedling trays after ten days from cuttage, and then spraying the solution once every seven days for accelerating tuberization; and

(10) harvesting the virus-free potato minitubers after 30–60 days of culturing.

2. The method according to claim 1, wherein said cuttaging seedlings are virus-free test tube plantlets aged 20–40 days.

3. The method according to claim 1, wherein said cuttaging seedlings are the new ones after cutting off the upper stem sections from said virus-free test tube plantlets and continuously culturing the lower stem sections with nodes on each in culture medium within test tubes for 18–20 days.

4. The method according to claim 1, wherein said cuttaging seedlings are the stem sections with 1–2 nodes on each cut from the seedlings grown 30 days after cuttage of virusfree seedling and cuttaging seedlings in claim 2.

5. The method according to claim 1, wherein said plant growth regulator aqueous solution contains 0.5 ppm GA-3, 20 ppm indolylbutyric acid and 3000 ppm $KH_2PO_4$.

6. The method according to claim 1, wherein the immersion period of said lower stem sections of cuttaging seedlings in said plant growth regulator solution is 10–15 minutes.

7. The method according to claim 1, wherein said nutrient solution consists of 10.3 g $KNO_3$, 1.7 g $NH_4NO_3$, 4.0 g $MgSO_4$, 3.5 g $KH_2PO_4$, 0.28 g $FeSO_4$, 0.37 g di-sodium EDTA and 1 g $Ca(NO_3)_2$ in every 10 liters and its pH value is 5.8.

8. The method according to claim 1, wherein said cuttage medium is a 1:1 mixture of vermiculite 4# and weed charcoal.

9. A method as claimed in claim 1 wherein the plantlet is a tip cutting have a growable point cut from plantlets which have been planted and grown in a greenhouse for 20 days.

* * * * *